United States Patent [19]

Yamada et al.

[11] Patent Number: 4,830,672
[45] Date of Patent: May 16, 1989

[54] ZIRCONIA-BASED COATING COMPOSITION

[75] Inventors: Kinji Yamada, Yokkaichi; Masaki Nagata, Yokohama; Siniti Suyama, Yokohama; Momoko Okamura, Yokohama, all of Japan

[73] Assignee: Japan Synthetic Rubber Co., Ltd., Tokyo, Japan

[21] Appl. No.: 156,825

[22] Filed: Feb. 17, 1988

[30] Foreign Application Priority Data

Feb. 24, 1987 [JP] Japan ................. 62-39084

[51] Int. Cl.$^4$ ............................................. C09K 3/00
[52] U.S. Cl. ............................ 106/287.19; 556/40
[58] Field of Search ................... 106/287.19; 556/40

[56] References Cited

U.S. PATENT DOCUMENTS

| | | | |
|---|---|---|---|
| 3,002,854 | 10/1961 | Brill | 556/40 |
| 3,017,282 | 1/1962 | Brill | 106/287.19 |
| 3,299,109 | 1/1967 | Sander | 556/40 |
| 4,609,745 | 9/1986 | Barfurth et al. | 556/40 |

*Primary Examiner*—Theodore Morris
*Attorney, Agent, or Firm*—Oblon, Fisher, Spivak, McClelland & Maier

[57] ABSTRACT

A zirconia-based coating composition comprising a mixture obtained by mixing:

(a) at least one compound selected from the group consisting of (a') a zirconium compound represented by the general formula (I):

$$Zr(OR)_4 \qquad (I)$$

wherein R is an alkyl group having 2-5 carbon atoms or the general formula (I'):

$$Zr(OR)_4 \cdot ROH \qquad (I')$$

wherein R has the same means as defined above, (a'') a partial hydrolyzate of the zirconium compound (a'), and (a''') a partial condensate of the partial hydrolyzate (a''), (b) a β-diketone or β-ketoester represented by the general formula (II):

$$R^1COOH_2COR^2 \qquad (II)$$

wherein $R^1$ is an alkyl group having 1-5 carbon atoms, $R^2$ is an alkyl group having 1-5 carbon atoms or an alkoxy group having 1-4 carbon atoms), (c) water, and (d) a hydrophilic organic solvent.

Said coating composition can form a transparent, very hard coating film on the surfaces of metals, inorganic building materials and plastics, can be hardened at low temperatures, can form a thick coating film, and can be recoated.

10 Claims, No Drawings

ZIRCONIA-BASED COATING COMPOSITION

BACKGROUND OF THE INVENTION

1. Field of the Invention

This invention relates to a zirconia-based coating composition which can form a transparent, very hard coating film on the surface of metals (e.g. stainless steel, aluminum and the like), inorganic building materials and plastics, can be hardened at low temperatures, can form a thick coating film, can be recoated, and can form a coating film superior in adhesion, corrosion resistance, insulating property, friction resistance, heat resistance, moisture resistance, weather resistance, flame resistance, water resistance, organic chemical resistance and acid resistance and particularly superior in alkali resistance.

2. Description of the Prior Art

In recent years, those coating compositions have been required which can be hardened at low temperatures, can form a thick coating film, can be recoated, and can form a very hard, transparent coating film superior in adhesion, corrosion resistance, insulating property, friction resistance, heat resistance, moisture resistance, weather resistance, flame resistance, water resistance, water impermeability, sea water resistance, organic chemical resistance, acid resistance, alkali resistance, etc.

As coating compositions satisfying only some of the above requirements, there have been proposed an aqueous acidic composition comprising a partial condensate of a silanol and colloidal silica (see U.S. Pat. Nos. 3,986,997 and 4,027,073) and a composition comprising a zirconium alkoxide or the like and a silicon compound having 1–4 alkoxy groups [see Japanese patent application Kokai (Laid-Open) No. 100,943/82].

However, the coating composition capable of forming a transparent coating film as stated in U.S. Pat. Nos. 3,986,997 and 4,027,073 has the following problems: The coating film formed is generally inferior in transparency, alkali resistance, storage stability and adhesion. When the film is as thin as about 20 μm, pin holes tend to be caused in the film. Even after the formulation, the ageing time till the composition becomes usable is long. The coating conditions are narrow. The workability is inferior. The wettability on organic coating film, plastics, etc. is inferior. The composition is difficult to recoat.

Further, the coating composition described in Japanese patent application Kokai (Laid-Open) No. 100,943/82 has the following problems: The composition is unable to form a thick coating film, inferior in storage stability, and liable to cause precipitation. Accordingly, it is difficult to prepare a uniform coating composition.

SUMMARY OF THE INVENTION

This invention has been made under such technical circumstances of prior art, and aims at providing a coating composition which has a good storage stability, can be hardened at low temperatures, can form a thick coating film, can be recoated, and can form a very hard, transparent coating film superior in adhesion, corrosion resistance, insulating property, friction resistance, heat resistance, moisture resistance, weather resistance, flame resistance, water resistance, organic chemical resistance, acid resistance, etc. and particularly superior in alkali resistance.

According to this invention, there is provided a coating composition comprising a mixture obtained by mixing:

(a) 1 mole (in terms of zirconium compound) of at least one compound selected from the group consisting of (a′) a zirconium compound represented by the general formula (I):

$$Zr(OR)_4 \tag{I}$$

wherein R is an alkyl group having 2–5 carbon atoms or the general formula (I′):

$$Zr(OR)_4 \cdot ROH \tag{I′}$$

wherein R has the same meaning as defined above, (a″) a partial hydrolyzate of the zirconium compound (a′), and (a‴) a partial condensate of the partial hydrolyzate (a″) [the zirconium compound, the partial hydrolyzate and the partial condensate are hereinafter collectively referred to as the component (a)], (b) 0.8–3 moles of a β-diketone or β-ketoester represented by the general formula (II):

$$R^1COCH_2COR^2 \tag{II}$$

wherein $R^1$ is an alkyl group having 1–5 carbon atoms, $R^2$ is an alkyl group having 1–5 carbon atoms or an alkoxy group having 1–4 carbon atoms [the β-diketone and β-ketoester are hereinafter collectively referred to as the component (b)], (c) 0.8–3 moles of water, and (d) 5–150 moles of a hydrophilic organic solvent.

DETAILED DESCRIPTION OF THE INVENTION

Each constituent of the present composition is described in detail.

Component (a)

The zirconium compound (a′) represented by the general formula (I), $Zr(OR)_4$ or the general formula (I′), $Zr(OR)_4 \cdot ROH$, used in this invention hydrolyzes in the presence of water to form a partial hydrolyzate (a″), and this partial hydrolyzate (a″) undergoes polycondensation to produce a partial condensate (a‴). When the present composition is formed into a coating film, the component (a) forms zirconia in the form of film.

R in the general formulas (I) and (I′) is an alkyl group having 2–5 carbon atoms such as ethyl, n-propyl, i-propyl, n-butyl, sec-butyl, t-butyl or the like.

Specific examples of the zirconium compound (a′) represented by the general formula (I) are zirconium tetraethoxide, zirconium tetra-n-propoxide, zirconium tetra-i-propoxide, zirconium tetra-n-butoxide, zirconium tetra-sec-butoxide and zirconium tetra-t-butoxide.

Specific examples of the zirconium compound (a′) represented by the general formula (I′) are zirconium tetraethoxide ethanolate, zirconium tetra-n-propoxide n-propanolate, zirconium tetra-i-propoxide i-propanolate, zirconium tetra-n-butoxide n-butanolate, zirconium tetra-sec-butoxide sec-butanolate, zirconium tetra-t-butoxide t-butanolate.

Of these zirconium compounds (a′), zirconium tetra-n-butoxide and zirconium tetra-n-butoxide n-butanolate is particularly preferable.

The component (a) may be used alone or in admixture of two or more.

Component (b)

The component (b) used in this invention is a β-diketone or β-ketoester represented by the general formula (II). The component (b) is believed to form a complex with the component (a) in the present composition to inhibit the formation of precipitate at the time of hydrolysis of the component (a).

In the general formula (II), $R^1$ is an alkyl group having 1-5 carbon atoms such as methyl, ethyl, n-propyl, i-propyl, n-butyl, sec-butyl, t-butyl or the like, and $R^2$ is an alkyl group having 1-5 carbon atoms (examples thereof are the same as in the case of $R^1$) or an alkoxy group having 1-4 carbon atoms such as methoxy, ethoxy, n-propoxy, i-propoxy, n-butoxy, sec-butoxy, t-butoxy or the like.

Specific examples of the component (b) are acetylacetone, methyl acetoacetate, ethyl acetoacetate, n-propyl acetoacetate, i-propyl acetoacetate, n-butyl acetoacetate, sec-butyl acetoacetate, t-butyl acetoacetate, 2,4-hexanedione, 2,4-heptanedione, 3,5-heptanedione, 2,4-octanedione, 2,4-nonanedione and 5-methyl-2,4-hexanedione.

Of these components (b), ethyl acetoacetate and acetylacetone are particularly preferable.

The component (b) may be used alone or in admixture of two or more.

The component (b) is used in a proportion of 0.8-3 moles, preferably 1-2 moles, more preferably 1-1.5 moles per mole (in terms of zirconium compound) of the component (a). When the proportion is less than 0.8 mole, the hydrolysis of the component (a) is so rapid that the precipitation is caused and the film formability is also inferior. When the proportion is more than 3 moles, the hydrolysis of the component (a) is so slow that the film formability and alkali resistance of the resulting composition are inferior.

Component (c)

Water which is the component (c) causes the hydrolysis of the component (a).

As the water, tap water, distilled water and deionized water may be used. When a coating composition having a high purity is desired, distilled water or deionized water is preferable and deionized water having an electrical conductance of 2 μS/cm or less is particularly preferable.

In order to prevent the violent hydrolysis of the component (a), it is preferable that the component (c) be mixed with the component (a) in the form of an organic solvent solution prepared by dissolving water in a hydrophilic organic solvent which is the component (d) so that the water content becomes not more than 30% by weight.

The component (c) is used in a proportion of 0.8-3 moles, preferably 1-2 moles per mole (in terms of zirconium compound) of the component (a). When the proportion is less than 0.8 mole, the hydrolysis of the component (a) is too slow, and hence, the resulting composition has an inferior film formability and an inferior alkali resistance. When the proportion is more than 3 moles, the hydrolysis of the component (a) is too rapid, and hence, the resulting composition has an inferior storage stability and an inferior film formability.

Component (d)

The hydrophilic organic solvent which is the component (d) mainly enables the components (a) to (c) to be uniformly mixed and further serves as an agent for controlling the concentration of the component (a). Also, the component (d) serves as an agent for controlling the hydrolysis velocity of the component (a) when the coating film formed on a substrate is hardened.

As said hydrophilic organic solvent, preferred are alcohols and low boiling hydrophilic organic solvents having a boiling point not higher than 120° C.

The alcohols include, for example, monohydric alcohols and dihydric alcohols.

Examples of the alcohols are methyl alcohol, ethyl alcohol, n-propyl alcohol, i-propyl alcohol, sec-butyl alcohol, t-butyl alcohol, n-pentyl alcohol, ethylene glycol monobutyl ether, ethylene glycol monoethyl ether acetate, and the like.

Examples of the low boiling hydrophilic organic solvents having a boiling point not higher than 120° C. are acetone, methyl ethyl ketone, tetrahydrofuran and the like.

Of these hydrophilic organic solvents, preferred are i-propyl alcohol, sec-butyl alcohol, n-propyl alcohol, n-butyl alcohol, ethylene glycol monoethyl ether acetate, etc. Particularly preferred are i-propyl alcohol and ethylene glycol monoethyl ether acetate.

These hydrophilic organic solvents may be used alone or in admixture of two or more.

The component (d) is used in a proportion of 5-150 moles, preferably 20-50 moles per mole (in terms of zirconium compound) of the component (a). When the proportion is less than 5 moles, the resulting composition has an inferior storage stability. When the proportion is more than 150 moles, the composition, though has a good storage stability, has too low a solids content and cannot form a thick film when coated, and the hardening of the coating film becomes insufficient because the amount of the component (a) hydrolyzed becomes small.

The composition of this invention can further comprise, if necessary, (e) at least one compound selected from the group consisting of (e') a titanium compound represented by the general formula (III):

$$Ti(OR^3)_p(R^1COCHCOR^2)_{4-p} \qquad (III)$$

wherein $R^3$ is an alkyl group having 1-5 carbon atoms, p is an integer of 2-4, and $R^1$ and $R^2$ have the same meanings as defined above, (e") a partial hydrolyzate of the titanium compound (e') and (e''') a partial condensate of the partial hydrolyzate (e") [the titanium compound, the partial hydrolyzate and the partial condensate are hereinafter collectively referred to as the component (e)], (f) at least one compound selected from the group consisting of (f') an aluminum compound represented by the general formula (IV):

$$Al(OR^3)_q(R^1COCHCOR^2)_{3-q} \qquad (IV)$$

wherein q is an integer of 2-3, and $R^1$, $R^2$ and $R^3$ have the same meaning as defined above, (f") a partial hydrolyzate of the aluminum compound (f') and (f''') a partial condensate of the partial hydrolyzate (f") [the aluminum compound, the partial hydrolyzate and the partial condensate are hereinafter collectively referred to as the component (f)], (g) an organosilane represented by the general formula (V):

$$R^4Si(OR^5)_3 \quad (V)$$

wherein $R^4$ is an organic group having 1–8 carbon atoms, and $R^5$ is an alkyl group having 1–5 carbon atoms or an acyl group having 1–4 carbon atoms, and (h) an organopolysiloxane having a structural unit represented by the general formula (VI):

$$R^6{}_aSiO_{(4-a)/2} \quad (VI)$$

wherein $R^6$ is an organic group having 1–8 carbon atoms, and a is an arbitrary number of 1.0–1.8 and further having in the molecule at least one —OX group bonded to the silicon atoms (X is a hydrogen atom or an alkyl group having 1–5 carbon atoms) [the organopolysiloxane is hereinafter referred to as the component (h)].

When the composition comprises the component (e) and/or the component (f), it is preferred that the component (c) is additionally added in an amount of 0.4–1 mole per equivalent of the —OR³ groups contained in the component (e) and/or the component (f) in order to allow the reaction of the component (e) and/or the component (f) to proceed.

In the general formula (III), $R^3$ is an alkyl group having 1–5 carbon atoms such as methyl, ethyl, n-propyl, i-propyl, n-butyl, sec-butyl, t-butyl or the like, and $R^1$ and $R^2$ are the same as in the case of the component (b).

Specific examples of the titanium compound (e′) represented by the general formula (III) are titanium dimethoxide bis(acetylacetonate), titanium diethoxide bis(acetylacetonate), titanium di-i-propoxide bis(acetylacetonate), titanium tetra-i-propoxide, titanium tetra-n-propoxide, titanium tetra-n-butoxide, titanium tetra-sec-butoxide, titanium tetra-n-pentoxide, titanium di-i-propoxide bis(ethylacetoacetate) and the like.

The partial condensate (e‴) of the partial hydrolyzate (e″) of the titanium compound (e′) can be obtained by hydrolyzing the titanium compound (e′) and subjecting the resulting partial hydrolyzate (e″) to polycondensation, and is soluble in the component (d).

Of these components (e), preferred are titanium di-i-propoxide bis(acetylacetonate), titanium tetra-i-propoxide, their partial hydrolyzates, and the partial condensates of these partial hydrolyzates.

These components (e) may be used alone or in admixture of two or more.

The component (e) is used in a proportion of not more than 3 moles per mole (in terms of zirconium compound) of the component (a). When the proportion is more than 3 moles, the coating film of the resulting composition tends to show inferior alkali resistance when hardened at low temperatures.

The aluminum compound (f′), together with the component (a), hydrolyzes in the presence of water into a partial hydrolyzate (f″), and this partial hydrolyzate (f″) undergoes polycondensation to produce a partial condensate (f‴). The partial condensate (f‴) becomes a higher molecular weight product by further polycondensation. When the present composition is formed into a coating film, the component (f) is hardened by heating the coating film at about 60° C. or allowing the coating film to stand at room temperature.

In the general formula (VI), $R^1$, $R^2$ and $R^3$ have the same meanings as in the case of the general formula (III).

Specific examples of the aluminum compound (f′) are aluminum dimethoxide acetylacetonate, aluminum diethoxide acetylacetonate, aluminum di-n-propoxide acetylacetonate, aluminum di-i-propoxide acetylacetonate, aluminum di-i-propoxide ethylacetoacetate, aluminum di-n-butoxide acetylacetonate, aluminum di-sec-butoxide acetylacetonate, aluminum di-t-butoxide acetylacetonate, aluminum di-n-pentoxide acetylacetonate, aluminum di-n-butoxide ethylacetoacetate, aluminum tri-i-propoxide, aluminum tri-n-propoxide, aluminum tri-sec-propoxide, aluminum tri-n-butoxide, aluminum tri-i-butoxide, aluminum tri-sec-butoxide, aluminum tri-n-pentoxide and the like.

The partial condensate (f‴) of the partial hydrolyzate (f″) of the aluminum compound (f′) can be obtained by hydrolyzing the aluminum compound (f′) to form the partial hydrolyzate (f″) and subjecting the partial hydrolyzate (f″) to polycondensation, and is soluble in the component (d).

Of these components (f), preferred are aluminum di-i-propoxide acetylacetonate, aluminum di-i-propoxide ethylacetoacetate, aluminum tri-n-propoxide, aluminum tri-sec-propoxide, their partial hydrolyzates, and partial condensates of these partial hydrolyzates.

These components (f) may be used alone or in admixture of two or more.

The component (f) is preferably used in a proportion of not more than 3 moles per mole (in terms of zirconium compound) of the component (a). When the proportion is more than 3 moles, the coating film of the resulting composition tends to show inferior alkali resistance when hardened at low temperatures.

The component (g) is an organosilane represented by the general formula (V).

When the component (g) is used, it is preferable that the component (c) be used together therewith in a proportion of $(0.8+b)$ to $(3+3b)$ [b is the number of moles of the component (g) used] per mole (in terms of zirconium compound) of the component (a).

In the general formula (V), $R^4$ is an organic group having 1–8 carbon atoms. It includes, for example, alkyl groups such as methyl, ethyl, n-propyl, i-propyl and the like; a γ-chloropropyl group; a vinyl group; a 3,3,3-trifluoropropyl group; a γ-glycidoxypropyl group; a γ-methacryloyloxypropyl a γ-mercaptopropyl group; a phenyl group; a 3,4-epoxycyclohexylethyl group; and a γ-aminopropyl group.

In the general formula (V), $R^5$ is an alkyl group having 1–5 carbon atoms or an acyl group having 1–4 carbon atoms and includes, for example, methyl, ethyl, n-propyl, i-propyl, n-butyl, sec-butyl, t-butyl, acetyl or the like.

Specific examples of the component (g) are methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-propyltriethoxysilane, γ-chloropropyltrimethoxysilane, γ-chloropropyltriethoxysilane, vinyltrimethoxysilane, vinyltriethoxysilane, 3,3,3-trifluoropropyltrimethoxysilane, 3,3,3-trifluoropropyltriethoxysilane, γ-glycidoxypropyltrimethoxysilane, γ-glycidoxypropyltriethoxysilane, γ-methacryloxypropyltrimethoxysilane, γ-methacryloxypropyltriethoxysilane, γ-mercaptopropyltrimethoxysilane, γ-mercaptopropyltriethoxysilane, phenyltrimethoxysilane, phenyltriethoxysilane, 3,4-epoxycyclohexylethyltrimethoxysilane, 3,4-epoxycyclohexylethyltriethoxysilane, etc. Of these, preferred are methyltrimethoxysilane and methyltriethoxysilane.

These components (g) may be used alone or in combination of two or more.

The component (g) preferably contains at least 80 mole % of $CH_3Si(OR^2)_3$.

The component (g) is preferably used in a proportion of 3–80 moles, more preferably 5–50 moles, most preferably 10–40 moles, per mole (in terms of zirconium compound) of the component (a). When the proportion is less than 3 moles, a gel is formed in some cases and cracks tend to occur in the hardened coating film. When it is more than 80 moles, the resulting hardened coating film has low alkali resistance.

The component (h) has a structural unit represented by the general formula (VI) and further has in the molecule at least one —OX group bonded to the silicon atoms.

In the general formula (VI), $R^6$ is an organic group having 1–8 carbon atoms. It includes, for example, alkyl groups such as methyl, ethyl, n-propyl, i-propyl and the like; a γchloropropyl group; a vinyl group; a 3,3,3-trifluoropropyl group; a γ-glycidoxypropyl group; a γ-methacryloxypropyl group; a γ-mercaptopropyl group; a phenyl group; a 3,4-epoxycyclohexylethyl group; and a γ-aminopropyl group. Of these organic groups, preferred are a methyl group and a phenyl group.

In the general formula (VI), a is an arbitrary number of 1.0–1.8, preferably 1.2–1.6. When a is less than 1.0, the coating film of the resulting composition causes cracking in some cases. When a is more than 1.8, it is difficult to harden the coating film in some cases.

The component (h) has in the molecule at least one, preferably 3–30 —OX groups bonded to the silicon atoms.

In the —OX group, X is a hydrogen atom or an alkyl group having 1–5 carbon atoms such as methyl, ethyl, n-propyl, i-propyl, n-butyl, sec-butyl, t-butyl or the like.

When the component (h) has no —OX group bonded to the silicon atoms, the hardening reaction of the composition does not proceed sufficiently in some cases.

The component (h) are silicones such as Silicone Varnishes TSR 116, TSR 108, TSR 117, TSR 144, TSR 145, YR 3187, TSR 147, TSR 160, TSR 165 and TSR 127B (these are products of TOSHIBA SILICONE K.K.) and Silicone Varnishes SH 804, SH 805, SH 806A, SH 808, SH 840, SR 2107, SR 2108 and SR 2400 (these are products of TORAY SILICONE K.K.)

As the component (h), there may be used organopolysiloxanes obtained by the hydrolysis and polycondensation of the componeng (g).

These components (h) may be used alone or in combination of two or more.

The proportion of the component (h) in the present composition is preferably 200–5,000 g, more preferably 500–3,000 g, per mole (in terms of zirconium compound) of the component (a). When the proportion is less than 200 parts by weight, the coating film of the resulting composition tends to have cracks when a thick coating film is formed. When the proportion is more than 5,000 parts by weight, the hardenability of the composition at low temperatures becomes low and the organic chemical resistance and weather resistance of the coating film are deteriorated.

The composition of this invention may further contain various additives such as surfactants; silane coupling agents; alkali metal salts of naphthenic acid, octylic acid, nitrous acid, sulfurous acid, aluminic acid, carbonic acid and the like; dyes; etc.

The composition of this invention comprising the components (a) to (d) can be produced preferably by (1) mixing the component (a), the component (b) and, if necessary, the component (d) and then (2) mixing the resulting mixture with the component (c) and the component (d).

In the step (1), the components (a) and (b) are mixed to prepare a liquid mixture. In this case, it is preferable that the resulting liquid mixture be allowed to stand for at least 15 minutes at room temperature. When the period of time for allowing the liquid mixture of the components (a) and (b) to stand at room temperature is less than 15 minutes, a precipitate is in some cases caused upon adding the component (c) in the step (2).

In the step (2), component (c) and the component (d) are added to the liquid mixture obtained in the step (1) to subject the mixture to hydrolysis and polycondensation.

When it is intended to mix the composition of this invention with the further optional component (e) and/or component (f), it is desirable that the component (e) and/or the component (f) be added to the mixture of the component (a) and the component (b), and the resulting mixture be allowed for at least 15 minutes at room temperature, after which the mixture is mixed with a solution of the component (c) in the component (d).

When the composition of this invention is intended to be mixed with the still further optional component (g) and/or component (h), the component (g) and/or the component (h) is added in the step (3) to the mixture having added thereto the component (c) and the component (d) in the step (2), and then in the step (4), the component (c) and, if necessary, the component (d) are added thereto.

In the step (2), it is preferable that after addition of the component (c), the resulting mixture be stirred for at least 15 minutes at room temperature.

Also in the step (3) wherein the reaction mixture obtained in the step (2) is mixed with the component (g) and/or the component (h) for further reaction, it is also preferable that after addition of the component (g) and/or the component (h), the resulting mixture be stirred for at least 15 minutes at room temperature.

In the step (4), the component (c) is additionally added to subject the components (a) and (g), particularly the component (g), to hydrolysis and polycondensation.

The proportion of the component (c) used in the step (4) is 1–3 moles, preferably 1.2–2 moles, per mole of the component (g). When the proportion is less than 1 mole, the hydrolysis and polycondensation becomes insufficient and the coating film provided by the resulting composition has lower alkali resistance. When the proportion is more than 3 moles, said reaction takes place violently and, in some cases, gelation occurs.

After the completion of the above steps, the resulting mixture may be aged by heating and stirring at 60°–80° C. for 1–10 hours.

The coating composition of this invention can be coated on the surface of an object substrate (e.g. stainless steel, aluminum, concrete, glass, plastic, paper, organic coating film, inorganic coating film or the like) by a coating means such as brushing, spraying, dipping or the like, in a film thickness of about 0.1–2 μm in single coating when the composition consists of only the components (a) to (d), of about 0.1–5 μm in single coating when the composition further comprises the component (e) and/or the component (f), of about 0.1–15 μm in single coating when the composition furthermore comprises the component (g), and of about 0.1–30 μm in single coating when the composition further comprises even the component (h). The coating film is, immediately or after natural drying, heat-dried, for example, at about 600°–300° C. for about 10–60 minutes to harden the same. It is possible to recoat the composition on the thus formed coating film.

DESCRIPTION OF PREFERRED EMBODIMENT OF THE INVENTION

This invention will be explained in more detail below referring to Examples. However, this invention should not be interpreted to be restricted to these Examples.

In the Examples, parts and % are by weight unless otherwise specified.

In the Examples, various measurements were conducted as follows:

Polystyrene-reduced weight average molecular weight

Measured according to gel permeation chromatography (GPC) under the following conditions:

A sample was prepared by dissolving 1 g of an organosilane condensate in 100 cc of tetrahydrofuran as a solvent.

The standard polystyrene was a standard polystyrene manufactured by Pressure Chemical Co., U.S.A.

Apparatus: Model 150-C ALC/GPC, a high temperature, high speed gel permeation chromatograph manufactured by Waters Co., U.S.A.

Column: SHODEX A-80M (length: 50 cm) manufactured by Showa Denko K.K.

Measurement temperature: 40° C.

Flow rate: 1 cc/min

Storage stability

A sample containing no hardening accelerator was stored in a tightly stoppered polyethylene bottle for one month at room temperature and the occurrence of gelation in the sample was examined visually. When the sample caused no gelation, the sample after storage was measured for viscosity in accordance with JIS K 5400 and, when the viscosity change was 10% or less, the storage stability of the sample was indicated as "no change".

Alkali resistance (1)

1 ml of a 1% aqueous sodium hydroxide solution was dropped on a coating film formed on a substrate. The substrate was then allowed to stand for 1 day in a petri dish with a lid and water-rinsed, after which the condition of the coating film was observed to evaluate the alkali resistance (1) of the coating film.

Alkali resistance (2)

1 ml of a 10% aqueous sodium hydroxide solution was dropped on a coating film formed on a substrate. The substrate was then allowed to stand for 1 day in a petri dish with a lid and water-rinsed, after which the condition of the coating film was observed to evaluate the alkali resistance (2) of the coating film.

Water resistance

Tap water was placed in a petri dish with a lid. Therein was immersed a substrate having a coating film formed thereon for 60 days, after which the condition of the coating film was observed to evaluate the water resistance of the coating film.

Organic chemical resistance

Toluene was placed in a petri dish. Therein was immersed a substrate having a coating film formed thereon for 60 days at room temperature, after which the condition of the coating film was observed to evaluate the organic chemical resistance of the coating film.

Moisture resistance

A coating film formed on a substrate was kept for a continuous period of 1,000 hours at a temperature of 50° C. at a humidity of 95%, after which the condition of the coating film was observed to evaluate the moisture resistance of the coating film.

Weather resistance

A coating film formed on a substrate was subjected to an irradiation test according to JIS K 5400 for 5,000 hours in a weatherometer, after which the condition of the coating film was observed to evaluate the weather resistance of the coating film.

Appearance of coating film

A coating film formed on a substrate was observed visually and by a stereoscopic microscope (magnification: 100) to evaluate the appearance of the coating film.

Hardness

Evaluated according to the pencil hardness specified by JIS K 5400.

Adhesion

A sample was subjected to a 1 mm×1 mm crosscut adhesive test specified by JIS K 5400 and then a scotch tape peeling test was conducted to evaluate the adhesion of the sample.

Heat resistance

A coating film formed on a substrate was kept in an electric furnace at 400° C. for 100 hours and then allowed to cool naturally, after which the condition of the coating film was observed to evaluate the heat resistance of the coating film.

Acid resistance (1)

1 ml of 20% hydrochloric acid was dropped on a coating film formed on a substrate. The substrate was then allowed to stand for 1 day in a petri dish with a lid and water-rinsed, after which the condition of the coating film was observed to evaluate the acid resistance (1) of the coating film.

Acid resistance (2)

1 ml of 20% sulfuric acid was dropped on a coating film formed on a substrate. The substrate was then allowed to stand for 1 day in a petri dish with a lid and water-rinsed, after which the condition of the coating film was observed to evaluate the acid resistance (2) of the coating film.

Examples 1 to 3 and Comparative Examples 1 to 7

In order to examine the properties of the present composition and the coating film formed therefrom, three compositions A to C as shown in Table 1 were prepared (Examples 1 to 3).

In the preparation of these compositions, the component (a), the component (b) and the component (d) were stirred in a polyethylene bottle with a cap for 30 minutes at room temperature; to the resulting mixture was added a mixture of the component (c) and the component (d) [the weight ratio of the component (c) to the total of the component (c) and the component (d)=5/100]; and then, they were stirred for 1 hour at room temperature.

For comparison with the effect of this invention, compositions D to J as shown in Table 1 were also prepared (Comparative Examples 1 to 7) in the same manner as in the case of the compositions A to C.

Subsequently, a soda-lime glass plate of $50 \times 50 \times 1$ mm was dipped in each of the compositions A to J and, after having been taken out, it was dried at 150° C. for 20 minutes. The same procedure was repeated, whereby a coating was conducted two times in total. Each of the thus prepared test pieces was subjected to various tests. The results obtained are shown in Table 1.

Separately, an aluminum plate of $100 \times 100 \times 2$ mm meeting JIS H 4000, A2024P was subjected to spray-coating with each of the compositions A to J and dried at 150° C. for 30 minutes. Each of the thus prepared test pieces was subjected to various tests. The results obtained are shown in Table 1.

EXAMPLES 4 to 9

In order to examine the properties of the present composition and the coating film formed therefrom, six compositions A' to F' as shown in Table 2 were prepared (Examples 4 to 9).

In the preparation of these compositions, the component (a), the component (b), the component (d) and the component (e) were stirred in a polyethylene bottle with a cap for 30 minutes at room temperature; to the resulting mixture was added a mixture of the component (c) and the component (d) [the weight ratio of the component (c) to the total of the component (c) and the component (d)≐25/75]; and then, they were stirred for 1 hour at room temperature.

Subsequently, a steel plate of $50 \times 50 \times 1$ mm meeting JIS G 3141, SPCC-B was dipped in each of the compositions A' to F' and, after having been taken out, it was dried at 60° C. for 30 minutes or at 150° C. for 30 minutes. The same procedure was repeated, whereby coating was conducted two times in total. Each of the thus prepared test pieces was subjected to various tests. The results obtained are shown in Table 2.

Examples 10 to 12

In order to examine the properties of the present composition and the coating film formed therefrom, three compositions A" to C" as shown in Table 3 were prepared (Examples 10 to 12).

In the preparation of these compositions, the component (a), the component (b), the component (d) and the component (f) were stirred in a polyethylene bottle with a cap for 30 minutes at room temperature; to the resulting mixture was added a mixture of the component (c) and the component (d) [the weight ratio of the component (c) to the total of the component (c) and the component (d)=25/75]; and then, they were stirred for 1 hour at room temperature.

Subsequently, a steel plate of $50 \times 50 \times 1$ mm meeting JIS G 3141, SPCC-B was dipped in each of the compositions A" to C" and, after having been taken out, it was dried at 60° C. for 30 minutes to obtain three kinds of test pieces.

These test pieces were subjected to various tests. The results obtained are shown in Table 3.

Separately, an aluminum plate meeting JIS H 4000, A1030P was spray-coated with each of the compositions A" to C" and then dried at 60° C. for 30 minutes. The test pieces thus prepared were subjected to various tests. The results obtained are shown in Table 3.

Reference Example 1 (Preparation of organosilane condensate h-1)

In a reactor equipped with a reflux condenser and a stirrer were placed 1 mole of methyltrimethoxysilane and 1.8 moles of water. They were heated for 2 hours at 60° C. to react them, after which 2 moles of i-propyl alcohol was added to obtain an organosilane condensate h-1.

The organosilane condensate h-1 had a polystyrene-reduced weight average molecular weight of 1,100.

Reference Example 2 (Preparation of organosilane condensate h-2)

In the same reactor as in Reference Example 1 were placed 0.9 mole of methyltrimethoxysilane, 0.1 mole of phenyltrimethoxysilane and 1.8 moles of water. They were subjected to reaction at 60° C. for 4 hours, after which 2 moles of i-propyl alcohol was added to obtain an organosilane condensate h-2.

The organosilane condensate h-2 had a polystyrene-reduced weight average molecular weight of 1,300.

Examples 13 to 19 and Comparative Examples 17 to 18

In order to examine the properties of the present composition and the coating film formed therefrom, compositions K to Q (Examples 13 to 19) and compositions R to S (Comparative Examples 17 to 18) were prepared by use of the materials, proportions and mixing methods shown in Table 4.

Subsequently, each of these compositions K to Q and R to S was spray-coated on a degreased aluminum plate meeting JIS H 4000, A2024P and then dried at 150° C. for 20 minutes. The test pieces thus prepared were subjected to various tests. The results obtained are shown in Table 4.

Examples 20 to 27 and Comparative Examples 19 to 23

In order to examine the properties of the present composition and the coating film formed therefrom, compositions K' to R' (Examples 20 to 27) and compositions S' to W' (Comparative Examples 19 to 23) were prepared by use of the materials, proportions and mixing methods shown in Table 5. These compositions were evaluated for appearance and storage stability.

Subsequently, each of these compositions K' to R' and S' to W' was mixed with other components as shown in Table 6 to prepare new compositions. Each of the new compositions was spray-coated on an aluminum plate meeting JIS H 4000, A2024P and then dried at 150° C. for 30 minutes. The test pieces thus prepared were subjected to various tests. The results obtained are shown in Table 6.

TABLE 1

| Composition | Example 1 A | Example 2 B | Example 3 C | Comparative Example 1 D | Comparative Example 2 E | Comparative Example 3 F | Comparative Example 4 G | Comparative Example 5 H | Comparative Example 6 I | Comparative Example 7 J |
|---|---|---|---|---|---|---|---|---|---|---|
| Proportions (moles) of materials charged | | | | | | | | | | |
| (a) Zirconium tetra-n-butoxide | 0.1 | 0.1 | 0.1 | 0.1 | 0.1 | 0.1 | 0.1 | 0.1 | 0.1 | 0.1 |
| (b) Methyl acetoacetate | 0.1 | — | — | — | — | — | — | — | — | — |
| (b) Acetylacetone | — | 0.1 | — | — | — | — | — | — | — | — |
| (b) Ethyl acetoacetate | — | — | 0.1 | — | 0.1 | 0.1 | 0.6 | 0.01 | 0.1 | 0.1 |
| (c) Water (deionized) | 0.1 | 0.1 | 0.1 | 0.1 | 0.6 | 0.01 | 0.1 | 0.1 | 0.1 | 0.1 |
| (d) i-Propyl alcohol | 3 | 3 | 3 | 3 | 3 | 3 | 3 | 3 | 15 | 0.2 |
| Storage stability of composition | No change | No change | No change | Precipitation | Precipitation | No change | No change | Precipitation | No change | Gelation after 3 days |
| Evaluation results of composition on a glass plate | | | | | | | | | | |
| Film thickness (μm) | 2 | 2 | 2 | — | — | ↑ | ↑ | — | 0.1 | — |
| Appearance of coating film | No change | No change | No change | — | — | ↑ | ↑ | — | — | — |
| Hardness | 4H | 4H | 5H | — | — | No film formation | No film formation | — | 3B | — |
| Adhesion | 100/100 | 100/100 | 100/100 | — | — | ↓ | ↓ | — | Poor | — |
| Heat resistance | No change | No change | No change | — | — | ↓ | ↓ | — | " | — |
| Acid resistance (1), (2) | No change | No change | No change | — | — | ↓ | ↓ | — | " | — |
| Alkali resistance (1), (2) | No change | No change | No change | — | — | ↓ | ↓ | — | " | — |
| Water resistance | No change | No change | No change | — | — | ↓ | ↓ | — | " | — |
| Organic chemical resistance | No change | No change | No change | — | — | ↓ | ↓ | — | " | — |
| Moisture resistance | No change | No change | No change | — | — | ↓ | ↓ | — | " | — |
| Weather resistance | No change | No change | No change | — | — | ↓ | ↓ | — | " | — |
| Evaluation results of composition on an aluminum plate | | | | | | | | | | |
| Film thickness (μm) | 3 | 3 | 3 | — | — | ↑ | ↑ | — | 0.2 | — |
| Appearance of coating film | No change | No change | No change | — | — | ↑ | ↑ | — | — | — |
| Hardness | 2H | 2H | 2H | — | — | ↑ | ↑ | — | 4B | — |
| Adhesion | 100/100 | 100/100 | 100/100 | — | — | ↑ | ↑ | — | Poor | — |
| Acid resistance (1), (2) | No change | No change | No change | — | — | ↑ | ↑ | — | " | — |
| Alkali resistance (1), (2) | No change | No change | No change | — | — | No film formation | No film formation | — | " | — |
| Water resistance | No change | No change | No change | — | — | ↓ | ↓ | — | " | — |
| Organic Chemical resistance | No change | No change | No change | — | — | ↓ | ↓ | — | " | — |
| Moisture resistance | No change | No change | No change | — | — | ↓ | ↓ | — | " | — |
| Weather resistance | No change | No change | No change | — | — | ↓ | ↓ | — | " | — |

TABLE 2

| Composition | Example 4 A' | Example 5 B' | Example 6 C' | Example 7 D' | Example 8 E' | Example 9 F' |
|---|---|---|---|---|---|---|
| Proportions (moles) of materials charged | | | | | | |
| (a) Zirconium tetra-n-butoxide | 0.1 | 0.1 | 0.1 | 0.1 | 0.1 | 0.1 |
| (b) Ethyl acetoacetate | — | 0.125 | 0.2 | — | 0.2 | — |
| (b) Acetylacetone | 0.11 | — | — | 0.25 | — | 0.125 |
| (c) Water (deionized) | 0.11 | 0.125 | 0.2 | 0.25 | 0.33 | 0.25 |
| (d) i-Propyl alcohol | 3.33 | 3.75 | 6 | 7.5 | 10 | 3.75 |
| (e) Titanium di-i-propoxide bis(acetylacetonate) | 0.011 | 0.025 | 0.1 | 0.15 | 0.23 | 0.025 |
| Storage stability of composition | No change | No change | No change | No change | No change | No change |
| Evaluation results of composition hardened at 60° C. for 30 min. | | | | | | |
| Film thickness (μm) | 4 | 5 | 4 | 4 | 5 | 4 |
| Appearance of coating film | No change | No change | No change | No change | No change | No change |
| Hardness | 5H | 5H | 5H | 5H | 5H | 5H |
| Adhesion | 100/100 | 100/100 | 100/100 | 100/100 | 100/100 | 100/100 |
| Heat resistance | No change | No change | No change | No change | No change | No change |
| Acid resistance (1), (2) | " | " | " | " | " | " |
| Alkali resistance (1), (2) | " | " | " | " | " | " |

TABLE 2-continued

| Composition | Example 4 A' | Example 5 B' | Example 6 C' | Example 7 D' | Example 8 E' | Example 9 F' |
|---|---|---|---|---|---|---|
| Water resistance | " | " | " | " | " | " |
| Organic chemical resistance | " | " | " | " | " | " |
| Moisture resistance | " | " | " | " | " | " |
| Weather resistance | " | " | " | " | " | " |
| Evaluation results of composition hardened at 150° C. for 30 min. | | | | | | |
| Film thickness (μm) | 4 | 5 | 4 | 4 | 5 | 5 |
| Appearance of coating film | No change | No change | No change | No change | No change | No change |
| Hardness | 5H | 5H | 5H | 5H | 5H | 5H |
| Adhesion | 100/100 | 100/100 | 100/100 | 100/100 | 100/100 | 100/100 |
| Heat resistance | No change | No change | No change | No change | No change | No change |
| Acid resistance (1), (2) | " | " | " | " | " | " |
| Alkali resistance (1), (2) | " | " | " | " | " | " |
| Water resistance | " | " | " | " | " | " |
| Organic chemical resistance | " | " | " | " | " | " |
| Moisture resistance | " | " | " | " | " | " |
| Weather resistance | " | " | " | " | " | " |

TABLE 3

| Composition | Example 10 A'' | Example 11 B'' | Example 12 C'' |
|---|---|---|---|
| Proportions (moles) of materials charged | | | |
| (a) Zirconium tetra-n-butoxide | 0.1 | 0.1 | 0.1 |
| (b) Acetylacetone | 0.1 | 0.12 | 0.1 |
| (c) Water (deionized) | 0.2 | 0.2 | 0.3 |
| (d) i-Propyl alcohol | 6 | 6 | 6 |
| (f) Aluminum di-n-butoxide ethyl acetoacetate | 0.1 | 0.1 | 0.1 |
| Storage stability of composition | No change | No change | No change |
| Evaluation results of composition on a steel plate | | | |
| Film thickness (μm) | 5 | 4 | 4 |
| Appearance of coating film | No change | No change | No change |
| Hardness | 5H | 6H | 7H |
| Adhesion | 100/100 | 100/100 | 100/100 |
| Heat resistance | No change | No change | No change |
| Acid resistance (1), (2) | " | " | " |
| Alkali resistance (1), (2) | " | " | " |
| Water resistance | " | " | " |
| Organic chemical resistance | " | " | " |
| Moisture resistance | " | " | " |
| Weather resistance | " | " | " |
| Evaluation results of composition on an aluminum plate | | | |
| Film thickness (μm) | 5 | 5 | 4 |
| Appearance of coating film | No change | No change | No change |
| Hardness | 6H | 6H | 6H |
| Adhesion | 100/100 | 100/100 | 100/100 |
| Heat resistance | No change | No change | No change |
| Acid resistance (1), (2) | " | " | " |
| Alkali resistance (1), (2) | " | " | " |
| Water resistance | " | " | " |
| Organic Chemical resistance | " | " | " |
| Moisture resistance | " | " | " |
| Weather resistance | " | " | " |

TABLE 4

| Composition | Example 13 K | Example 14 L | Example 15 M | Example 16 N | Example 17 O | Example 18 P | Example 19 Q | Comparative Example 17 R | Comparative Example 18 S |
|---|---|---|---|---|---|---|---|---|---|
| Proportions of materials charged and mixing method | | | | | | | | | |
| step (1) Stirring for 30 min. at room temp. | | | | | | | | | |
| (a) Zirconium tetra-n-butoxide (mole) | 0.1 | 0.1 | 0.1 | 0.1 | 0.1 | 0.1 | 0.1 | 0.1 | 0.1 |
| (b) Ethyl acetoacetate (mole) | 0.1 | 0.1 | 0.1 | 0.1 | 0.1 | 0.1 | 0.1 | 0.1 | 0.1 |
| step (2) Stirring for 30 min. at room temp. | | | | | | | | | |
| (c) Water (mole) | 0.1 | 0.1 | 0.1 | 0.1 | 0.1 | 0.1 | 0.1 | 0.1 | 0.1 |
| (d) i-Propyl alcohol (mole) | 0.57 | 0.57 | 0.57 | 0.57 | 0.57 | 0.5 | 0.57 | 0.57 | 0.57 |
| step (3) Stirring for 30 min. at room temp. | | | | | | | | | |
| (g) Methyltrimethoxysilane (mole) | 2.0 | 1.3 | 1.5 | 2.0 | — | — | — | — | — |
| (g) Phenyltrimethoxysilane (mole) | — | 0.2 | — | — | — | — | — | — | — |
| (h) h-1 (part) | — | — | — | — | — | 170 | — | — | — |
| (h) h-2 (part) | — | — | — | — | 300 | — | — | — | — |
| (h) TSR 145*[1] (part) | 100 | 100 | — | — | — | — | 200 | 20 | 1,000 |
| (h) TSR 160*[2] (part) | — | — | 160 | — | — | — | — | — | — |
| (h) TSR 127B*[3] (part) | — | — | — | 200 | — | — | — | — | — |
| (d) Ethyl cellosolve (mole) | — | — | — | — | — | — | 2.4 | 1.2 | 10 |
| step (4) Stirring for 2 hr at room temp. | | | | | | | | | |
| (c) Water (moles) | 2.4 | 2.0 | 1.9 | 3.2 | — | — | — | — | — |
| (d) Ethyl cellosolve (moles) | — | — | 7.6 | 9.6 | — | — | — | — | — |
| (d) i-Propyl alcohol (moles) | 7.2 | 8.0 | — | — | — | — | — | — | — |
| Storage stability of composition | ← No change → | | | | ← Uniform and transparent → | | | Gelation after 10 min | No change |
| Evaluation results of composition on an aluminum plate | | | | | | | | | |
| Film thickness (μm) | 24 | 22 | 29 | 25 | 15 | 14 | 24 | 12 | 24 |
| Appearance of coating film | ← Transparent and no change → | | | | | | | | |
| Hardness | 4H | 3H | 4H | 3H | 5H | 5H | 3H | H | 2B |
| Adhesion | ← 100/100 → | | | | | | | ← 95/100 → | |

TABLE 4-continued

| Composition | Example 13 K | Example 14 L | Example 15 M | Example 16 N | Example 17 O | Example 18 P | Example 19 Q | Comparative Example 17 R | Comparative Example 18 S |
|---|---|---|---|---|---|---|---|---|---|
| Heat resistance | | | ← No change → | | ← No change → | | | ← Cracks appeared → | |
| Acid resistance (1), (2) | | | | | | | | | |
| Alkali resistance (1) | | | ← No change →  | | | | | Cracks appeared | Whitening |
| Alkali resistance (2) | | | ← No change → | | | | | ← Cracks appeared → | |
| Water resistance | | | ← No change → | | | | | ← Whitening → | |
| Organic chemical resistance | | | ← No change → | | | | | Cracks appeared | Film Dissolved |
| Weather resistance | | | ← No change → | | | | | Cracks appeared | Gloss reduced |

Note:
*1 to *3 Products of TOSHIBA SILICONE K.K. each having an organopolysiloxane content of 60%.

TABLE 5

| Composition | Example 20 K' | Example 21 L' | Example 22 M' | Example 23 N' | Example 24 O' | Example 25 P' | Example 26 Q' | Example 27 R' |
|---|---|---|---|---|---|---|---|---|
| Proportions (moles) of charged materials and mixing method | | | | | | | | |
| step (1) Stirring for 30 min at room temp. | | | | | | | | |
| (a) Zirconium tetra-n-butoxide | 1 | 1 | 1 | 1 | 1 | 1 | 1 | 1 |
| (b) Acetylacetone | 1 | — | — | — | — | — | — | — |
| (b) Ethyl acetoacetate | — | 1 | 1 | 1 | 1 | 1 | 1.8 | 1.2 |
| step (2) Stirring for 30 min at room temp. | | | | | | | | |
| (c) Water (deionized) | 1 | 1 | 2 | 3 | 1 | 1 | 1 | 2 |
| (d) i-Propyl alcohol | — | 19 | 18 | 17 | 19 | 19 | 19 | 18 |
| step (3) Stirring for 30 min at room temp. | | | | | | | | |
| (g) Methyltrimethoxysilane | 20 | 20 | 20 | 20 | 10 | 40 | 15 | 12 |
| (g) Phenyltrimethoxysilane | — | — | — | — | — | — | — | 3 |
| step (4) Stirring for 2 hr at room temp. | | | | | | | | |
| (c) Water (deionized) | 35 | 35 | 35 | 35 | 15 | 60 | 30 | 30 |
| Appearance of composition | | | ← No gel content → | | | | | |
| | | | ← Uniform and transparent → | | | | | |
| Storage stability of composition | | | ← No change → | | | | | |

| Composition | Comparative Example 19 S' | Comparative Example 20 T' | Comparative Example 21 U' | Comparative Example 22 V' | Comparative Example 23 W' |
|---|---|---|---|---|---|
| Proportions (moles) of charged materials and mixing method | | | | | |
| step (1) Stirring for 30 min at room temp. | | | | | |
| (a) Zirconium tetra-n-butoxide | 1 | 1 | 1 | 1 | 1 |
| (b) Acetylacetone | — | — | — | — | — |
| (b) Ethyl acetoacetate | 1 | 1 | 1 | 1 | 1 |
| step (2) Stirring for 30 min at room temp. | | | | | |
| (c) Water (deionized) | — | 1 | 1 | 1 | 1 |
| (d) i-Propyl alcohol | — | 19 | 19 | 19 | 19 |
| step (3) Stirring for 30 min at room temp. | | | | | |
| (g) Methyltrimethoxysilane | 20 | 2 | 100 | 15 | 15 |
| (g) Phenyltrimethoxysilane | — | — | — | — | — |
| step (4) Stirring for 2 hr at room temp. | | | | | |
| (c) Water (deionized) | 36 | 4 | 180 | 13 | 50 |
| Appearance of composition | Large amount of gel appeared | | ← No gel content → | | |
| | | | ← Uniform and transparent → | | |
| Storage stability of composition | — | Gelation after 1 week | — | — | Gelation after 3 days |

TABLE 6

| | Example 20 | Example 21 | Example 22 | Example 23 | Example 24 | Example 25 | Example 26 | Example 27 | Comparative Example 21 | Comparative Example 22 |
|---|---|---|---|---|---|---|---|---|---|---|
| Proportions (parts) of materials in coating composition | | | | | | | | | | |
| Composition (kind) | 100 (K') | 100 (L') | 100 (M') | 100 (N') | 100 (O') | 100 (P') | 100 (Q') | 100 (R') | 100 (U') | 100 (V') |
| i-Propanol | 60 | 60 | 80 | 60 | 40 | 10 | 50 | 60 | 50 | 50 |
| Methyl cellosolve | — | — | 20 | 60 | 10 | 70 | — | — | — | — |
| BM-1000*1 | — | 0.2 | — | 0.3 | — | — | — | — | — | — |
| Evaluation results of coating composition | | | | | | | | | | |
| Film thickness (μm) | 7 | 8 | 10 | 8 | 10 | 11 | 8 | 7 | 7 | 8 |
| Appearance of coating film | | | | ← Transparent and no change → | | | | | | |
| Hardness | 4H | 3H | 4H | 3H | 3H | 4H | 3H | 4H | 2B | 3B |
| Adhesion | | | | ← 100/100 → | | | | | | |

TABLE 6-continued

|  | Example 20 | Example 21 | Example 22 | Example 23 | Example 24 | Example 25 | Example 26 | Example 27 | Comparative Example 21 | Comparative Example 22 |
|---|---|---|---|---|---|---|---|---|---|---|
| Heat resistance | ← No change → | | | | | | | | ← Cracks appeared → | |
| Acid resistance (1), (2) | ← No change → | | | | | | | | | |
| Alkali resistance (1) | ← No change → | | | | | | | | | |
| Alkali resistance (2) | ← No change → | | | | | | | | ← Film dissolved → | |
| Water resistance | ← No change → | | | | | | | | | |
| Organic chemical resistance | ← No change → | | | | | | | | ← Film dissolved → | |
| Moisture resistance | ← No change → | | | | | | | | | |
| Weather resistance | ← No change → | | | | | | | | | |

Note:
*[1]Fluorine-containing surfactant manufactured by BM-CHMIE CO.

What is claimed is:

1. A zirconia-based coating composition comprising a mixture obtained by mixing:
   (a) 1 mole (in terms of zirconium compound) of at least one compound selected from the group consisting of (a') a zirconium compound represented by the general formula (I):

$$Zr(OR)_4 \qquad (I)$$

wherein R is an alkyl group having 2–5 carbon atoms or the general formula (I'):

$$Zr(OR)_4 \cdot ROH \qquad (I')$$

wherein R has the same meaning as defined above, (a'') a partial hydrolyzate of the zirconium compound (a'), and (a''') a partial condensate of the partial hydrolyzate (a''),
   (b) 0.8–3 moles of a β-diketone or β-ketoester represented by the general formula (II):

$$R^1COCH_2COR^2 \qquad (II)$$

wherein $R^1$ is an alkyl group having 1–5 carbon atoms, $R^2$ is an alkyl group having 1–5 carbon atoms or an alkoxy group having 1–4 carbon atoms,
   (c) 0.8–3 moles of water, and
   (d) 5–150 moles of a hydrophilic organic solvent.

2. The coating composition according to claim 1, wherein the component (a) is a mixture of (a') a zirconium compound of the general formula (I) or (I'), (a'') a partial hydrolyzate of the zirconium compound (a') and (a''') a partial condensate of the zirconium compound (a').

3. The coating composition according to claim 2, wherein the component (a) is at least one compound selected from the group consisting of zirconium tetraethoxide, zirconium tetra-n-propoxide, zirconium tetra-i-propoxide, zirconium tetra-n-butoxide, zirconium tetra-sec-butoxide and zirconium tetra-t-butoxide.

4. The coating composition according to claim 2, wherein the component (a) is zirconium tetraethoxide ethanolate, zirconium tetra-n-propoxide n-propanolate, zirconium tetra-i-propoxide i-propanolate, zirconium tetra-n-butoxide n-butanolate, zirconium tetra-sec-butoxide sec-butanolate or zirconium tetra-t-butoxide t-butanolate.

5. The coating composition according to claim 1, wherein the component (b) is at least one compound selected from the group consisting of acetylacetone, methyl acetoacetate, ethyl acetoacetate, n-propyl acetoacetate, i-propyl acetoacetate, n-butyl acetoacetate, t-butyl acetoacetate, 2,4-hexanedione, 2,4-heptanedione, 3,5-heptanedione, 2,4-octanedione, 2,4-nonanedione and 5-methylhexanedione.

6. The coating composition according to claim 1, wherein the component (d) is a monohydric alcohol or an dihydric alcohol.

7. The coating composition according to claim 6, wherein the component (d) is at least one compound selected from the group consisting of i-propyl alcohol, sec-butyl alcohol, n-propyl alcohol, n-butyl alcohol and ethylene glycol monoethyl ether acetate wherein said molar quantities are relative to each other.

8. The zirconia-based coating composition according to claim 1, wherein the proportion of the (b) component is 1 to 2 moles per mole of the (a) component in terms of the zirconium compound.

9. The zirconia-based coating composition according to claim 1, wherein the proportion of the (c) component is 1 to 2 moles per mole of the (a) component in terms of the zirconium compound.

10. The zirconia-based coating composition according to claim 1, wherein the proportion of the (d) component is 20 to 50 moles per mole of the (a) component in terms of the zirconium compound.

* * * * *